(12) United States Patent
Wang et al.

(10) Patent No.: US 11,826,395 B2
(45) Date of Patent: Nov. 28, 2023

(54) METHODS FOR PREPARATION OF PLECTRANTHUS AMBOINICUS EXTRACTS

(71) Applicant: Oneness Biotech Co., Ltd., Taipei (TW)

(72) Inventors: Yueh-Ju Wang, Taipei (TW); Kung-Ming Lu, Taipei (TW)

(73) Assignee: ONENESS BIOTECH CO., LTD., Taipei (TW)

( * ) Notice: Subject to any disclaimer, the term of this patent is extended or adjusted under 35 U.S.C. 154(b) by 0 days.

(21) Appl. No.: 17/849,924

(22) Filed: Jun. 27, 2022

(65) Prior Publication Data
US 2023/0000941 A1    Jan. 5, 2023

Related U.S. Application Data

(60) Provisional application No. 63/215,697, filed on Jun. 28, 2021.

(51) Int. Cl.
| | | |
|---|---|---|
| A61K 36/53 | (2006.01) | |
| A61K 31/352 | (2006.01) | |
| A61K 31/216 | (2006.01) | |
| A61K 31/05 | (2006.01) | |

(52) U.S. Cl.
CPC .............. *A61K 36/53* (2013.01); *A61K 31/05* (2013.01); *A61K 31/216* (2013.01); *A61K 31/352* (2013.01); *A61K 2236/333* (2013.01); *A61K 2236/37* (2013.01); *A61K 2236/51* (2013.01); *A61K 2236/53* (2013.01)

(58) Field of Classification Search
None
See application file for complete search history.

(56) References Cited

U.S. PATENT DOCUMENTS

2013/0131159 A1    5/2013  Ko et al.

FOREIGN PATENT DOCUMENTS

| CN | 101139291 A | | 3/2008 |
|---|---|---|---|
| KR | 20090022998 A | * | 3/2009 |
| TW | 200724150 A | | 7/2007 |
| TW | 200908990 A | | 3/2009 |
| TW | I535449 B | | 6/2016 |
| TW | 201811352 A | | 4/2018 |

\* cited by examiner

*Primary Examiner* — Michael V Meller
(74) *Attorney, Agent, or Firm* — McDermott Will & Emery LLP

(57) ABSTRACT

A method for preparing a *Plectranthus amboinicus* (PA) extract, the method comprising extracting an above-ground part of *Plectranthus amboinicus* with an extracting solution that comprises a solvent having a suitable polarity index, filtrating and concentration the extract thus produced, and subject the concentrated extract to a chromatographic separation process using a hydrophobic interaction chromatography resin to produce the PA extract.

19 Claims, No Drawings

METHODS FOR PREPARATION OF *PLECTRANTHUS AMBOINICUS* EXTRACTS

CROSS REFERENCE TO RELATED APPLICATIONS

This application claims the benefit of the filing date of U.S. Provisional Application No. 63/215,697, filed Jun. 28, 2021, the entire contents of which are incorporated by reference herein.

BACKGROUND OF THE INVENTION

*Plectranthus amboinicus* (also known as *Coleus amboinicus* Lour., *Coleus aromaticus* Benth., *Coleus aromaticus* auct., *Plectranthus aromaticus* Roxb., *Plectranthus aromaticus* Benth., and *Plectranthus amboinicus* (Lour.) Spreng.), is a perennial medicinal herb of the Lamiaceae (also known as Labiatae) family native to Southern and Eastern Africa. *Plectranthus amboinicus* is also known as patchouli, Cuban oregano, Indian borage, Indian mint, Mexican mint, Mexican oregano, country borage, and Spanish thyme.

*Plectranthus amboinicus* has various health benefits, for example, antimicrobial activity, antifungal activity, anti-inflammatory activity, antidiabetic activity, anxiolytic activity, antineoplastic, analgesic, antimalarial, antibiofilm efficacy, diuretic, wound healing activity, skincare, respiratory disorders, and antiplatelet aggregation activity. *Plectranthus amboinicus* is reported to contain several classes of phytochemicals, including monoterepenoids, diterpenoids, triterpenoids, sesquiterpenoids, phenolics, flavonoids and esters. Different preparation processes result in *Plectranthus amboinicus* extracts having different combinations of phytochemicals at different concentrations, thereby possessing different health benefits.

SUMMARY OF THE INVENTION

The present disclosure is based, at least in part, on the development of preparation processes for producing *Plectranthus amboinicus* (PA) extracts having desired active components, e.g., effective in promoting wound healing. Such preparation processes substantially shorten the whole preparation process with high yields.

Accordingly, the present disclosure provides a method for preparing a *Plectranthus amboinicus* (PA) extract, the method comprising: (i) mixing an above-ground part of *Plectranthus amboinicus* with an extracting solution to produce a first PA extract, wherein the extracting solution comprises a solvent having a polarity index of about 2.9 to 6.6; (ii) filtrating and optionally concentrating the first PA extract to produce a second PA extract, which optionally is a concentrated PA extract; (iii) contacting the second PA extract (e.g., the concentrated PA extract) onto a hydrophobic interaction chromatography resin, and (iv) eluting the column with a eluent solution to product the PA extract, wherein the eluent solution comprises a solvent having a polarity index of about 2.1-5.4.

In some embodiments, the solvent in the extracting solution in step (i) can be acetone, butyl methyl ether, ethanol, ethyl acetate, isopropyl alcohol, methanol, or a mixture thereof. In some examples, the solvent in the extracting solution is ethanol. In other examples, the solvent in the extracting solution is ethyl acetate. In still other examples, the solvent in the extracting solution is acetone. Alternatively, the solvent in the extracting solution is isopropyl alcohol. In other examples, the solvent in the extracting solution can be methanol.

In some instances, step (i) can be repeated 2-4 times, optionally 2 times. In some instances, step (i) can be performed at a temperature of about 25-80° C. (e.g., about 40-80° C. or about 50-80° C.) for about 1-9 hours (e.g., 1-3 hours). Alternatively, step (i) is performed at a temperature of about 20-30° C. for about 12-48 hours (e.g., 12-24 hours or 24-48 hours). In some examples, the weight-to-volume ratio between the above-ground part of *Plectranthus amboinicus* and the extracting solution in step (i) may be about 1:10 to about 1:20 (kg/liter).

In some embodiments, in step (ii), the first PA extract can be concentrated to reduce the volume to about 30%-70% (e.g., about 30-50%) of the original volume to produce the concentrated PA extract. In other embodiments, the first PA extract can be concentrated to reduce the volume to about 2.5% to about 4% of the original volume to produce the concentrated PA extract.

In other embodiments, step (ii) does not involve concentrating the first PA extract.

In some embodiments, the hydrophobic interaction chromatography resin used in step (iii) can be a non-polar copolymer styrene-divynilbenzene adsorbent resin, a polystyrene polymer cross linked with divinylbenzene, or a polystyrene divinyl-benzene copolymer resin. In some instances, step (iii) can be performed by loading the concentrated PA extract onto a column comprising the hydrophobic interaction chromatography resin. Alternatively, step (iii) can be performed by mixing the concentrated PA extract with the hydrophobic interaction chromatography resin.

In some embodiments, the eluent solution in step (iv) may comprise a mixture of at least two solvents selected from the group consisting of acetone, ethanol, ethyl acetate, isopropyl alcohol, and hexane. In some instances, the eluent solution may comprise two of the solvents at a 50:50 ratio by volume. In one example, the elution solution contains a mixture of hexane and ethyl acetate. In another example, the elution solution contains a mixture of ethanol and ethyl acetate. In yet another example, the elution solution contains a mixture of acetone and ethyl acetate. In still another example, the elution solution contains a mixture of acetone and isopropyl alcohol.

Any of the methods disclosed herein may further comprise, prior to step (iv) and after step (iii), washing the hydrophobic interaction chromatography resin with an aqueous solution comprising ethanol.

Also provided herein is a *Plectranthus amboinicus* (PA) extract, which is prepared by any method disclosed herein. In some instances, the PA extract may comprise salvigenin, cirsimaritin, rosmarinic acid, and carvacrol. In some examples, a PA extract prepared by a method disclosed herein may comprise 0.04%-0.4% salvigenin (w/w), 0.01%-0.9% cirsimaritin (w/w), up to 1.1% rosmarinic acid (w/w), and 0.04%-6.7% carvacrol (w/w).

The details of one or more embodiments of the invention are set forth in the description below. Other features or advantages of the present invention will be apparent from the following drawings and detailed description of several embodiments, and also from the appended claims.

DETAILED DESCRIPTION OF THE INVENTION

*Plectranthus amboinicus* is a medicinal plant with numerous pharmacological properties. Different preparation processes lead to *Plectranthus amboinicus* (PA) extracts having different combinations of phytochemical components at different concentrations, leading different biological activities and thus medicinal utilities.

Provided herein are processes for producing PA extracts containing phytochemical components with desired therapeutic activities, for example, wound healing. Such processes exhibit one or more advantageous features, such as high yields and shortened preparation time. Accordingly, the preparation processes disclosed herein can product PA extracts with high efficiency for use in making pharmaceutical composition with desired therapeutic utilities, e.g., prompting wound healing.

I. Preparation of *Plectranthus amboinicus* (PA) Extracts

In some aspects, the present disclosure provides methods for preparing *Plectranthus amboinicus* extracts using an above-ground part of a *Plectranthus amboinicus* plant as the starting material. The above-ground part may comprise leaves, stems, flowers, or a combination thereof. In some examples, the whole above-ground of a *Plectranthus amboinicus* plant can be used as the starting material. The above-ground part of a *Plectranthus amboinicus* plant can be fresh. Alternatively, the above-ground part of a *Plectranthus amboinicus* plant can be in dried form. In some instances, the above-ground part of a *Plectranthus amboinicus* plant can be dried to form powders, which can be used as the starting material for preparing the *Plectranthus amboinicus* extracts disclosed herein, which are also within the scope of the present disclosure.

Any of the preparation methods disclosed herein may comprise at least the following steps: (i) extraction step, (ii) filtration and concentration step, (iii) separation step via hydrophobic interaction chromatography, and (iv) elution step. In some instances, the methods may further comprise a washing step between the separation steps (iii) and the elution step (iv).

(a) Extraction Step

The extraction step may be performed by mixing an above-ground part of a *Plectranthus amboinicus* plant (e.g., those disclosed above) with an extracting solution, which comprises a solvent with a suitable polarity index. Polarity index of a solvent refers to the relative measure of the degree of interaction of a solvent with various polar test solutes. Table 1 below lists commonly used solvents and their polarity index (Snyder polarity index).

TABLE 1

Exemplary Solvents and Their Polarity Index

| Solvent | Polarity Index (Snyder) |
|---|---|
| cyclohexane | 0 |
| n-hexane | 0 |
| n-decane | 0.3 |
| i-octane | 0.4 |
| octane | 0.4 |
| butyl ether | 1.7 |
| carbon tetrachloride | 1.7 |
| triethyl amine | 1.8 |
| i-propyl ether | 2.2 |
| toluene | 2.3 |
| xylene, p- | 2.4 |
| t-butyl methyl ether | 2.9 |
| benzene | 3 |
| benzyl ether | 3.3 |
| dichloromethane | 3.4 |
| methylene chloride | 3.4 |
| chloroform | 3.4-4.4 |
| dichloroethane | 3.7 |

TABLE 1-continued

Exemplary Solvents and Their Polarity Index

| Solvent | Polarity Index (Snyder) |
|---|---|
| ethylene dichloride | 3.7 |
| butanol, 1- | 3.9 |
| i-butyl alcohol | 3.9 |
| tetrahydrofuran | 4.2 |
| ethyl acetate | 4.3 |
| propanol, 1- | 4.3 |
| propanol, 2- | 4.3 |
| methyl acetate | 4.4 |
| cyclohexanone | 4.5 |
| methyl ethyl ketone (MEK) | 4.5 |
| nitrobenzene | 4.5 |
| benzonitrile | 4.6 |
| dioxane, 1,4- | 4.8 |
| dioxane, p | 4.8 |
| ethanol | 5.2 |
| nitroethane | 5.3 |
| pyridine | 5.3 |
| acetone | 5.4 |
| benzyl alcohol | 5.5 |
| methoxyethanol, 2- | 5.7 |
| acetic acid | 6.2 |
| acetonitrile | 6.2 |
| dimethyl formamide, N,N- | 6.4 |
| dimethyl sulfoxide | 6.5 |
| methanol | 6.6 |
| formamide | 7.3 |
| water | 9 |

In some instances, a solvent having a polarity index ranging from about 2.9 to about 6.6 can be used in the extraction step. In some instances, the solvent can be a single solvent (i.e., containing a homogenous population of solvent compounds, e.g., ethanol). In other instances, the solvent can be a co-solvent (i.e., containing a mixture of multiple solvent compounds, e.g., a mixture of ethanol and acetone).

The suitable solvent for use in the extraction step may be any of the solvent in Table 1 having a polarity index of 2.9 to 6.6, or a mixture thereof. In some examples, the solvent can be ethanol. In other examples, the solvent can be acetone. In yet other examples, the solvent can be a mixture of ethanol and acetone (e.g., 1:1 ratio by volume). Other suitable solvents include t-butyl methyl ether, ethyl acetate, isopropyl alcohol, methanol, or a mixture thereof.

In some instances, the above-ground part of a *Plectranthus amboinicus* plant may be mixed with any of the suitable solvent disclosed herein at a ratio of about 1:10 to 1:20 (kg/Liter). For example, 1 kg of the above-ground part of a *Plectranthus amboinicus* plant can be placed in 10-20 liter of the solvent. The mixture can be stirred for a suitable period (e.g., 1 hour to 24 hours) at a suitable temperature (e.g., room temperature to 80° C.). In some examples, the extraction step may be carried out at an elevated temperature, for example at 60±5° C. In this case, the extraction period may be shortened, for example, to about 1 hour to 2 hours (e.g., about 90 minutes). Alternatively, the extraction step may be carried out at room temperature, for example, at about 20-25° C. In that case, the extraction period may take about 12 hours to 24 hours. In other examples, the extraction step may be carried out at about 30-40° C. for about 3-8 hours (e.g., 4 hours).

Any of the extraction steps disclosed herein may be repeated multiple times, for example, 2 times.

(b) Filtration and Optional Concentration Step

In some instances, the crude extract obtained from an extraction step as disclosed herein may be filtered to remove solid components.

In some embodiments, either the crude extract or the resultant filtrate may be concentrated by a conventional method, e.g., vacuum concentration. In some examples, the volume of the concentrated extract can be reduced to about 1%-70% of the original volume (of the crude extract or the filtrate). In some examples, the crude extract or the filtrate can be concentrated at a low level, for example, the volume of the concentrated extract may be about 30%-70% (e.g., about 30-50%) of the volume before concentration (original volume). In other examples, the crude extract or filtrate may be concentrated at a high level, for example, about 2%-10% volume reduction. In some examples, the volume of the concentrated extract may be about 2-4% of the volume before concentration (original volume).

Alternatively, the crude extract or the resultant filtrate may not be substantially concentrated (volume reduction is less than 20%, e.g., less than 15%, 10%, or 5%) or no concentration at all.

(c) Separation Steps

The concentrated crude extract obtained from the filtration and concentration step can then be subject to separation via hydrophobic interaction chromatography, which separates components in the concentrated crude extract according to their differences in surface hydrophobicity. This step can be performed by contacting the concentrated solution with a hydrophobic interaction chromatography resin, which can be any non-ionic and hydrophobic resin. Examples include, but are not limited to, non-polar copolymer styrene-divynilbenzene adsorbent resin (e.g., DIAION® HP20, DIAION® HP20SS, AMBERLITE® XAD-2 or AMBERLITE® XAD-4), a nonionic and cross-linked polymeric adsorbent resin (SEPLITE® LX20), or a polystyrene divinyl-benzene copolymer resin (e.g., Amberlite™ XAD1180N). Other examples include methacrylate-based resin, silica gel, nonionic polystyrene-divinylbenzene polymer resin (e.g., SEPABEAD® SP27).

In some examples, the hydrophobic interaction chromatography resin may be packed in a column, which may be washed for equilibration before loading of the materials for separation. The concentrated solution can then be loaded onto and pass through the column. In some examples (e.g., high level concentrated crude extract), the column can be washed sequentially by one or more solutions after loading. The solutions for sequential wash may comprise a solvent having high to low polarity index. For example, the column may be first washed by water, followed by 50% ethanol (in water), and then by ethanol. Alternatively, the resin may be washed by a solvent having low polarity index, for example, hexane. In other examples, the wash step may not be necessary, for example, for low level concentrated crude extract.

In other examples, a concentrated solution may be mixed with a hydrophobic interaction chromatography resin. After being stirred for a suitable period, the mixture can be filtrated to remove the supernatant. In some instances (e.g., high level concentrated crude extract), the resin can then be washed sequentially by one or more solutions after loading via mixing and stirring the resins in the solution. The solutions for sequential wash may comprise a solvent having high to low polarity indexes. For example, the resins may be first washed by water, followed by 50% ethanol (in water), and then by ethanol. Alternatively, the resin may be washed by a solvent having low polarity index, for example, hexane. In other examples, the wash step may not be necessary, for example, for low level concentrated crude extract.

(d) Elution Step

The resins, either packed in a column or in mixture with the concentrated crude extract, can then be eluted using a suitable eluent solution to provide the *Plectranthus amboinicus* (PA) extract of interest. The eluent solution may contain a solvent having a suitable polarity index, for example, about 2.1 to about 5.4. In some examples, a solvent having a polarity index of 4.3-5.4 can be used. In some examples, the solvent can be a single solvent. In other instances, the solvent can be a co-solvent. Examples of the solvent for use in the eluent solution include, but are not limited to, a mixture of ethanol and ethyl acetate (e.g., at a ratio of 1:1 or 2:1 by volume), a mixture of acetone and ethyl acetate (e.g., at a ratio of 1:1 or 2:1 by volume), a mixture of hexane and ethyl acetate (e.g., at a ratio of 1:1). Other solvents having similar polarity index as these examples can also be used in the elution solution.

(e) Exemplary Extraction Procedures

Table 2 below provides exemplary solvents and conditions for each step of the extraction procedures disclosed herein. These exemplary conditions are provided for illustration purposes only.

TABLE 2

Exemplary Solvents and Conditions Used in PA Extract Preparation Processes

| Steps | Regents and Conditions | Examples |
|---|---|---|
| Extraction | Solvent: Polarity Index (PI) of about 2.9 to 6.6 | Ethanol (PI: 5.2) Ethyl acetate (PI: 4.3) Acetone (PI: 5.4) Isopropyl alcohol (PI: 4.3) Methanol (PI: 6.6) |
| | Temperature: 25-80° C. | 25 ± 2° C. 40 ± 2° C. 60 ± 5° C. |
| | Period: 1-9 hours | 1 hr 2 hr 3 hr |
| | Time: 2-4 times | 1 time 2 time 3 time |
| Concentration | Yes No | Up to 6-fold concentration |
| Separation | Resin: a non-polar copolymer styrene-divinylbenzene adsorbent resin, a nonionic and cross-linked polymeric adsorbent resin, a polystyrene divinyl-benzene copolymer resin, or $SiO_2$ | HP20 LX-20 XAD1180N Silica gel |
| | Means of separation | Loading Binding Stirring |
| Elution | Eluent: solvent with PI of about 2.1-5.4 | hexane and ethyl acetate ethanol and ethyl acetate acetone and ethyl acetate acetone and isopropyl alcohol |

The fractions eluted using any of the eluent solutions disclosed herein can be collected, which are the PA extracts containing phytochemical components (e.g., salvigenin) with desired bioactivities (e.g., promoting wound healing).

II. Pharmaceutical Compositions Comprising *Plectranthus amboinicus* (PA) Extracts The *Plectranthus amboinicus* (PA) extract prepared by any of the methods disclosed herein can be mixed with a pharmaceutically acceptable carrier (excipient) to form a pharmaceutical composition for the therapeutic uses disclosed herein. "Acceptable" means that the carrier must be compatible with the active ingredient of the composition (and preferably, capable of stabilizing the active ingredient) and not deleterious to the subject to be treated. Pharmaceutically acceptable excipients (carriers) including buffers, which are well known in the art. See, e.g., Remington: The Science and Practice of Pharmacy 20th Ed. (2000) Lippincott Williams and Wilkins, Ed. K. E. Hoover.

The pharmaceutical compositions to be used in the present methods can comprise pharmaceutically acceptable carriers, excipients, or stabilizers in the form of lyophilized formulations or aqueous solutions. (Remington: The Science and Practice of Pharmacy 20th Ed. (2000) Lippincott Williams and Wilkins, Ed. K. E. Hoover). Acceptable carriers, excipients, or stabilizers are nontoxic to recipients at the dosages and concentrations used, and may comprise buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrans; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG).

The pharmaceutical compositions to be used for in vivo administration must be sterile. This is readily accomplished by, for example, filtration through sterile filtration membranes. Therapeutic compositions are generally placed into a container having a sterile access port, for example, an intravenous solution bag or vial having a stopper pierceable by a hypodermic injection needle.

The pharmaceutical compositions described herein can be in unit dosage forms such as tablets, pills, capsules, powders, granules, solutions or suspensions, or suppositories, for oral, parenteral or rectal administration, or for topical administration.

For preparing solid compositions such as tablets, the principal active ingredient can be mixed with a pharmaceutical carrier, e.g., conventional tableting ingredients such as corn starch, lactose, sucrose, sorbitol, talc, stearic acid, magnesium stearate, dicalcium phosphate or gums, and other pharmaceutical diluents, e.g., water, to form a solid preformulation composition containing a homogeneous mixture of a compound of the present invention, or a non-toxic pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer that serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

Suitable surface-active agents include, in particular, non-ionic agents, such as polyoxyethylenesorbitans (e.g., Tween™ 20, 40, 60, 80 or 85) and other sorbitans (e.g., Span™ 20, 40, 60, 80 or 85). Compositions with a surface-active agent will conveniently comprise between 0.05 and 5% surface-active agent, and can be between 0.1 and 2.5%. It will be appreciated that other ingredients may be added, for example mannitol or other pharmaceutically acceptable vehicles, if necessary.

In some embodiments, the pharmaceutical composition disclosed herein, comprising the PA extract, may be a topical formulation, which can be used for promoting wound healing (e.g., the healing of wounds for diabetic patients). Such a topical formulation may comprises salvigenin in an amount ranging from about 0.0001% to about 0.5% (w/w), and optionally asiaticoside, which may be in an amount ranging from about 0.05% to about 5% (w/w). In some embodiments, asiaticoside may be contained in a *Centella asiatica* extract, or both in an amount of about 0.1-30% (w/w). See, e.g., U.S. Pat. No. 10,758,584, the relevant disclosures of which are incorporated by reference for the subject matter and purpose referenced herein.

The topical formulation may further comprise one or more carriers or excipients, including one or more of viscosity increasing agents (e.g., about 1.0-10%), one or more ointment bases (e.g., one or more cream base) which may range from about 5-30%, one or more antimicrobial preservative (e.g., about 0.005-0.2% by weight), one or more emulsifying agents (about 0.5-10% by weight) or a combination thereof. These components may be dissolved or disbursed in a suitable solvent.

The topical formulation further comprises one or more carriers and excipients, including viscosity increasing agents, ointment bases (e.g., cream bases), antimicrobial preservatives, emulsifying agents, and/or solvents.

A "viscosity increasing agent" is an agent that is used to thicken a formulation. Exemplary viscosity increasing agents may include, for example, cetostearyl alcohol, cholesterol, stearyl alcohol, chlorocresol, white wax, stearic acid, cetyl alcohol, or a combination thereof. The viscosity increasing agent may be present in the topical formation at a concentration of about 1.0-10% (w/w). For example, the topical formulation may comprise about 1-1.5%, 1.5-2%, 2-2.5%, 2.5-3%, 3-3.5%, 3.5-4%, 4-4.5%, 4.5-5%, 5-5.5%, 5.5-6%, 6-6.5%, 6.5-7%, 7-7.5%, 7.5-8%, 8-8.5%, 8.5-9%, 9-9.5%, or 9.5-10% (w/w) of the viscosity increasing agent. Alternatively, the topical formulation may comprise about 1-5%, 2.5-7.5%, or 5-10% (w/w) of the viscosity increasing agent.

An "ointment base" can be any semisolid preparation or vehicle into which an active agent may be incorporated. Exemplary ointment bases include, but are not limited to, oleaginous ointment bases (e.g., white petrolatum or white ointment), absorption ointment bases (e.g., hydrophilic petrolatum, anhydrous lanolin, Aquabase™, Aquaphor®, and Polysorb®), water/oil emulsion ointment bases (e.g., cold cream, hydrous lanolin, rose water ointment, Hydrocream™ Eucerin®, and Nivea®), oil/water emulsion ointment bases (e.g., hydrophilic ointments, Dermabase™, Velvachol®, and Unibase®), and water-miscible ointment bases (e.g., polyethylene glycol (PEG) ointment and Polybase™). Ointment bases may be pharmacologically inert but can entrap water in order to provide an emollient protective film. In a specific embodiment, the ointment base may be any petrolatum compound (e.g., petrolatum, white petrolatum, white soft paraffin, liquid petrolatum, liquid paraffin). In a further specific embodiment, the ointment base is white petrolatum (CAS number 8009-03-8). The ointment base may be present in the topical formation at a concentration of about 5-30% (w/w), e.g., 10-30% (w/w). For example, the topical formulation may comprise about 5-25%, 5-20%, 5-15%, 5-15%, 10-15%, 15-20%, 20-25%, or 25-30% (w/w) of the ointment base. Specifically, the topical formulation may comprise about 5, 6, 7, 8, 9, 10, 11, 12, 13, 14, 15, 16, 17, 18, 19, 20, 21, 22, 23, 24, 25, 26, 27, 28, 29, or 30 percent (w/w) of the ointment base.

In some embodiments, the "ointment base" described herein contains less than 20% water and volatiles, and more than 50% hydrocarbons, waxes, or polyols as the vehicle. In some embodiments, the "ointment base" described herein is a "cream base," which contains more than 20% water and volatiles and/or typically contain less than 50% hydrocarbons, waxes, or polyols as the vehicle for the drug substance. The cream base can be a multiphase preparation containing a lipophilic phase and an aqueous phase. In some instances, the cream base is a lipophilic cream base, which has a lipophilic phase as the continuous phase. Such a cream base usually contains water-in-oil emulsifying agents such as wool alcohols, sorbitan esters and monoglycerides. In other instances, the cream base is a hydrophilic cream base, which has an aqueous phase as the continuous phase. Such a cream base typically contains oil-in-water emulsifying agents such as sodium or trolamine soaps, sulfated fatty alcohols, polysorbates and polyoxyl fatty acid and fatty alcohol esters, which may be in combination with water-in-oil emulsifying agents, if needed.

An "antimicrobial preservative" can be any compound capable of destroying microbes, prevent the multiplication or growth of microbes, or prevent the pathogenic action of microbes. Exemplary antimicrobial preservatives include, but are not limited to, a paraben compound (an ester of para-hydroxybenzoic acid; e.g., paraben, methylparaben, ethylparaben, propylparaben, butylparaben, heptylparaben, benzylparaben, isobutylparaben, isopropylparaben, benzylparaben, or their sodium salts), benzalkonium chloride, benzethonium chloride, benzyl alcohol, boric acid, bronopol, cetrimide, cetylpyridinium chloride, chlorhexidine, chlorobutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, and thimerosal. The antimicrobial preservative may be present in the topical formation at a concentration of about 0.005-0.2%, e.g., about 0.01-0.2% (w/w). For example, the topical formulation may comprise about 0.005-0.01%, 0.01-0.05%, 0.05-0.1%, 0.1-0.15%, or 0.15-0.2% (w/w) of the antimicrobial preservative. Specifically, the topical formulation may comprise about 0.005, 0.006, 0.007, 0.008, 0.009, 0.01, 0.02, 0.03, 0.04, 0.05, 0.06, 0.07, 0.08, 0.09, 0.1, 0.11, 0.12, 0.13, 0.14, 0.15, 0.16, 0.17, 0.18, 0.19, or 0.2 percent (w/w) of the antimicrobial preservative.

An "emulsifying agent" is a compound or substance which acts as a stabilizer for a mixture of two or more liquids that are normally immiscible (unmixable or unblendable). Exemplary emulsifying agents may include, but are not limited to, natural emulsifying agents (e.g., acacia, agar, alginic acid, sodium alginate, tragacanth, chondrux, cholesterol, xanthan, pectin, gelatin, egg yolk, casein, wool fat, cholesterol, wax, and lecithin), colloidal clays (e.g., bentonite [aluminum silicate] and Veegum [magnesium aluminum silicate]), long chain amino acid derivatives, high molecular weight alcohols (e.g., stearyl alcohol, cetyl alcohol, oleyl alcohol, triacetin monostearate, ethylene glycol distearate, glyceryl monostearate, propylene glycol monostearate, and polyvinyl alcohol), carbomers (e.g., carboxy polymethylene, polyacrylic acid, acrylic acid polymer, and carboxyvinyl polymer), carrageenan, cellulosic derivatives (e.g., carboxymethylcellulose sodium, powdered cellulose, hydroxymethyl cellulose, hydroxypropyl cellulose, hydroxypropyl methylcellulose, and methylcellulose), sorbitan fatty acid esters (e.g., polyoxyethylene sorbitan monolaurate [Tween® 20], polyoxyethylene sorbitan [Tween® 60], polyoxyethylene sorbitan monooleate [Tween® 80], sorbitan monopalmitate [Span® 40], sorbitan monostearate [Span® 60], sorbitan tristearate [Span® 65], glyceryl monooleate, and sorbitan monooleate [Span® 80]), polyoxyethylene esters (e.g., polyoxyethylene monostearate [Myrj® 45], polyoxyethylene hydrogenated castor oil, polyethoxylated castor oil, polyoxymethylene stearate, and Solutol), sucrose fatty acid esters, polyethylene glycol fatty acid esters (e.g., Cremophor®), polyoxyethylene ethers (e.g., polyoxyethylene lauryl ether [Brij®]), and poly(vinyl-pyrrolidone), diethylene glycol monolaurate, triethanolamine oleate, sodium oleate, potassium oleate, ethyl oleate, oleic acid, ethyl laurate, sodium lauryl sulfate, Pluronic F 68, Poloxamer 188, cetrimonium bromide, cetylpyridinium chloride, benzalkonium chloride, and docusate sodium, and/or combinations thereof. The emulsifying agent may be present in the topical formation at a concentration of about 0.5-10% (w/w), e.g., 0.5-6% (w/w). For example, the topical formulation may comprise about 0.5-1%, 1-1.5%, 1.5-2%, 2-2.5%, 2.5-3%, 3-3.5%, 3.5-4%, 4-4.5%, 4.5-5%, 5-5.5%, 5.5-6%, 5-10%, 6-10%, or 8-10% (w/w) of the emulsifying agent. Specifically, the topical formulation may comprise about 0.5, 0.6, 0.7, 0.8, 0.9, 1, 1.5, 2, 2.5, 3, 3.5, 4, 4.5, 5, 5.5, 6, 6.5, 7, 7.5, 8, 8.5, 9, 9.5, or 10 percent (w/w) of the emulsifying agent.

The topical formulation disclosed herein may further contain one or more solvents (e.g., non-water solvents or water). Exemplary non-water solvents may include, but are not limited to, any known solvent including propylene glycol, glycol, and mixtures thereof. The non-water solvent may be present in the topical formation at a concentration of about 2-65% (w/w). For example, the topical formulation may comprise about 2-15%, 15-30%, 30-45%, or 45-65% (w/w) of the solvent. In some embodiments, the topical formulation of the invention may also contain water.

In some embodiments, the topical formulation may further comprise one or more emollients, fragrances, or pigments. The topical formula may also be used in conjunction with a wound dressing (e.g., bandage with adhesive, plaster patch and the like) (e.g., cyclohexane, n-hexane, n-decane, i-octane, octane, butyl ether, carbon tetrachloride, triethyl amine, i-propyl ether, toluene, p-xylene, t-butyl methyl ether, benzene, benzyl ether, dichloromethane, methylene chloride, chloroform, dichloroethane, ethylene dichloride, 1-butanol, i-butyl alcohol, tetrahydrofuran, ethyl acetate, 1-propanol, 2-propanol, methyl acetate, cyclohexanone, methyl ethyl ketone (MEK), nitrobenzene, benzonitrile, 1,4-dioxane, or p-dioxane).

III. Therapeutic Applications of Pharmaceutical Compositions Comprising *Plectranthus amboinicus* (PA) Extracts Any of the pharmaceutical compositions (e.g., topical formulations) comprising an effective amount of the PA extracts prepared by a method disclosed herein can be used for treating a target disease or conditions, for example, promoting wound healing, in a subject in need of the treatment via a suitable route, such as intravenous administration, e.g., as a bolus or by continuous infusion over a period of time, by intramuscular, intraperitoneal, intracerebrospinal, subcutaneous, intra-articular, intrasynovial, intrathecal, oral, inhalation or topical routes.

As used herein, "an effective amount" refers to the amount of each active agent required to confer therapeutic effect on the subject, either alone or in combination with one or more other active agents. Determination of whether an amount of the PA extract achieved the therapeutic effect would be evident to one of skill in the art. Effective amounts vary, as recognized by those skilled in the art, depending on the particular condition being treated, the severity of the condition, the individual patient parameters including age, physical condition, size, gender and weight, the duration of the treatment, the nature of concurrent therapy (if any), the specific route of administration and like factors within the knowledge and expertise of the health practitioner. These factors are well known to those of ordinary skill in the art and can be addressed with no more than routine experimentation. It is generally preferred that a maximum dose of the individual components or combinations thereof be used, that is, the highest safe dose according to sound medical judgment.

Empirical considerations, such as the half-life, generally will contribute to the determination of the dosage. For example, antibodies that are compatible with the human immune system, such as humanized antibodies or fully human antibodies, may be used to prolong half-life of the PA extract or the active components therein. Frequency of administration may be determined and adjusted over the course of therapy, and is generally, but not necessarily, based on treatment and/or suppression and/or amelioration and/or delay of a target disease/disorder.

In some embodiments, a topical formulation as disclosed herein may be applied to a wound site following a suitable dosage and treatment regimen. The dosage and administration regimen for the described method will depend on the nature and condition of the wound being treated, the age and condition of the patient, and any prior or concurrent therapy. In some instances, the topical formulation can be applied once every week, once every other day, once daily, twice daily, three times daily, or four time daily for a suitable period of time. The treatment may be terminated when the wound is recovered. When necessary, the treatment may resume, for example, if a wound recurs.

The term "wound" refers to an injury to living tissue caused by a cut, blow, or other impact (e.g., caused by a medical condition such as a skin disorder), typically one in which the skin is cut or broken. Wound may be associated with a medical condition, for example, a skin disorder. The term "wound healing" denotes the dynamic and complex process of replacing devitalized or missing cellular structures and/or tissue layers. The term "promotion of wound healing" or "promoting wound healing" denotes the inducement of an increased level or rate of replacement for devitalized or missing cellular structures and/or tissue layers. As an example, promotion of wound healing may be indicated by partial or complete ulcer closure or an increase in the healing rate of an ulcer (including but not limited to more rapid changes in ulcer size, area, or severity, a more rapid closure of the ulcer, and/or an increase in the percentage change from baseline in ulcer size, area, or severity when compared to a control ulcer treated with a placebo).

The subject to be treated by the topical formulation can be a human or a non-human mammal. In some embodiments, the subject is a human patient having an open wound, which refers to an injury or damage to living tissues (e.g., skin) that cause a disruption in the normal continuity of biological structures. An open wound may include, but is not limited to, an abrasion, incision, laceration, puncture, avulsion, cut, or other similar injuries.

In other embodiments, the subject is a human patient having a chronic wound, which can be injuries or damage to living tissues (e.g., skin) that cause a disruption in the normal continuity of biological structures and do not heal in an orderly set of stages and/or in a predictable amount of time. A chronic wound may include, but is not limited to: a surgical wound, a traumatic wound, a pressure ulcer, a venous ulcer, or a diabetic ulcer. In other examples, a chronic wound may be associated with a disease or disorder, for example, a carcinoma, burn, bedsore, a skin disorder such as atopic dermatitis.

In one example, the subject is a human patient having foot ulcer associated with diabetes (e.g., type I or type II). Diabetes mellitus (also known as diabetes) is a group of metabolic diseases which result in high blood sugar levels over a prolonged period. Diabetes may result from the pancreas not producing enough insulin or the cells of the body not responding properly to the insulin produced. The three main types of diabetes mellitus are Type I (also known as "insulin-dependent diabetes mellitus" (IDDM) or "juvenile diabetes"; results from the failure of the pancreas to produce enough insulin), Type 2 (also known as "non-insulin-dependent diabetes mellitus" (NIDDM) or "adult-onset diabetes"; results from the failure of cells to respond to insulin properly), and gestational diabetes (seen during pregnancy when high blood sugar levels are observed in the absence of a previous history of diabetes). Many serious complications are observed in diabetic patients including, but not limited to, chronic wounds such as diabetic foot ulcers (also known as diabetic ulcers).

In some embodiments, the subject to be treated by the methods described herein suffers from a severe wound, for example, having an ulcer with an area greater than 2 cm$^2$ (e.g., 3 cm$^2$, 4 cm$^2$ or 5 cm$^2$). In some examples, the subject suffers from one or more plantar ulcers Without further elaboration, it is believed that one skilled in the art can, based on the above description, utilize the present invention to its fullest extent. The following specific embodiments are, therefore, to be construed as merely illustrative, and not limitative of the remainder of the disclosure in any way whatsoever. All publications cited herein are incorporated by reference for the purposes or subject matter referenced herein.

Example 1: Exemplary *Plectranthus Amboinicus* Preparation Process A

For extraction, 1 kg of the above ground part of *Plectranthus amboinicus* was stirred in 10-20 L ethanol at 60±5° C. for 90 minutes. This step was repeated twice and the resultant mixture was filtered and concentrated using rotary evaporation until the volume of the concentrated extract was about 2.5%-4% of the original volume. The concentrated solution was diluted with water and loaded onto a column packed with DIAION® HP-20 resin (a non-polar copolymer styrene-divynilbenzene adsorbent resin). The column was washed with water and 50% ethanol, and ethanol sequentially. Afterwards, the column was eluted with an eluent containing ethanol and ethyl acetate at about 1:1 ratio (v/v). The eluted fraction was collected and dried to obtain a PA extract (yield: 1.0%)

Example 2: Exemplary *Plectranthus Amboinicus* Preparation Process B

For extraction, 1 kg of the above ground *Plectranthus amboinicus* was stirred in 10-20 L ethanol at 60±5° C. for 90 minutes. This step was repeated twice and the resultant mixture was filtered and concentrated using rotary evaporation until the volume of the concentrated extract was about 2.5%-4% of the original volume. The concentrated solution was diluted with water and then mixed with DIAION® HP-20 resin (a non-polar copolymer styrene-divynilbenzene adsorbent resin), which was then packed into a column. The column washed with water, 50% ethanol, and ethanol sequentially. The solid portion was then eluted by an eluent solution containing ethanol and ethyl acetate at a volume ration of about 1:1. The eluted fraction was collected and dried to obtain a PA extract (yield: 1.0%)

Example 3: Exemplary *Plectranthus Amboinicus* Preparation Process C

For extraction, 1 kg of the above ground part of *Plectranthus amboinicus* was stirred in 10-20 L ethanol at 60±5° C. for 90 minutes. This step was repeated twice and the resultant mixture was filtered and concentrated using rotary evaporation until the volume of the concentrated extract was about 2.5%-4% of the original volume. The concentrated solution was diluted with water then loaded onto a column packed with DIAION® HP-20 resin (a non-polar copolymer styrene-divynilbenzene adsorbent resin). The column was washed with water, 50% ethanol, and ethanol sequentially. Afterwards, the column was eluted with an eluent solution containing acetone and ethyl acetate at a volume ratio of about 1:1. The eluted fraction was collected and dried to product a PA extract (yield: 1.1%)

Example 4: Exemplary *Plectranthus Amboinicus* Preparation Process D

For extraction, 1 kg of the above ground part of *Plectranthus amboinicus* was stirred in 10-20 L ethanol at 60±5° C. for 90 minutes. This step was repeated twice and the resultant mixture was filtered and concentrated using rotary evaporation until the volume of the concentrated extract was about 2.5%-4% of the original volume. The concentrated solution was diluted with water and then mixed with DIAION® HP-20 resin (a non-polar copolymer styrene-divynilbenzene adsorbent resin), which was then packed into a column. The column was washed with water, 50% ethanol, and ethanol sequentially, and then eluted by an eluent solution containing acetone and ethyl acetate at a volume ratio of about 1:1. The eluted fraction was collected and dried to produce a PA extract (yield: 1.1%)

Example 5: Exemplary *Plectranthus Amboinicus* Preparation Process E

For extraction, 1 kg of the above ground part of *Plectranthus amboinicus* was stirred in 10-20 L ethanol at 60±5° C. for 90 minutes. This step was repeated twice and the resultant mixture was filtered and concentrated using rotary evaporation until the volume of the concentrated extract was about 30-70% of the original volume. Without dilution, the concentrated solution was loaded onto a column packed with DIAION® HP-20 resin (a non-polar copolymer styrene-divynilbenzene adsorbent resin). The column was eluted with an eluent solution containing ethanol and ethyl acetate at a volume ratio of about 1:1. The eluted fraction was collected and dried to produce a PA extract (yield: 1.2%).

Example 6: Exemplary *Plectranthus Amboinicus* Preparation Process F

For extraction, 1 kg of the above ground part of *Plectranthus amboinicus* was stirred in 10-20 L ethanol at room temperature (e.g., about 20-25° C.) for 24 hours. This step was repeated twice and the resultant mixture was filtered and concentrated using rotary evaporation until the volume of the concentrated extract was about 2.5%-4% of the original volume. The concentrated solution was diluted with water then loaded onto a column packed with DIAION® HP-20 resin (a non-polar copolymer styrene-divynilbenzene adsorbent resin). The column was washed with water, 50% ethanol, and ethanol sequentially. Afterwards, the column was eluted with an eluent solution containing ethanol and ethyl acetate at a volume ratio of about 1:1. The eluted fraction was collected and dried to produce a PA extract (yield: 0.4%).

Example 7: Exemplary *Plectranthus Amboinicus* Preparation Process G

For extraction, 1 kg of the above-ground part of *Plectranthus amboinicus* was stirred in 10-20 L ethanol at 60±5° C. for 90 minutes. This step was repeated twice and the resultant mixture was filtered and concentrated using vacuum to dry. The dried PA extract was then loaded onto a column packed with silica gel. The column was washed with hexane. Afterwards, the column was eluted with an eluent solution containing hexane and ethyl acetate at a volume ratio of about 1:1. The eluted fraction was collected and dried to produce a PA extract (yield: 1.4%).

Example 8: Exemplary *Plectranthus Amboinicus* Preparation Process H

For extraction, 1 kg of the above-ground part of *Plectranthus amboinicus* was stirred in 10-20 L ethanol at 60±5° C. for 90 minutes. This step was repeated twice and the resultant mixture was filtered and concentrated using vacuum concentration to dry. The dried PA extract was then loaded onto a column packed with HP-20 resin (a non-polar copolymer styrene-divynilbenzene adsorbent resin). The column was washed with hexane. Afterwards, the column was eluted with an eluent solution having hexane and ethyl acetate at a volume ratio of about 1:1. The eluted fraction was collected and dried to produce a PA extract (yield: 1.0%).

Example 9: Exemplary *Plectranthus Amboinicus* Preparation Process I

For extraction, 1 kg of the above-ground part of *Plectranthus amboinicus* was stirred in 10-20 L ethanol at 60±5° C. for 90 minutes. This step was repeated twice and the resultant mixture was filtered and concentrated using rotary evaporation until the volume of the concentrated extract was about 30-70% of the original volume. Without dilution, the concentrated solution was then loaded onto a column packed with LX-20 resin (a nonionic, hydrophobic, polystyrene polymer, cross linked with divinylbenzene). The column was eluted with an eluent solution containing ethanol and ethyl acetate at a volume ratio of about 1:1. The eluted fraction was collected and dried to produce a PA extract (yield: 1.2%)

Example 10: Exemplary *Plectranthus Amboinicus* Preparation Process J

For extraction, 1 kg of the above-ground part *Plectranthus amboinicus* was stirred in 10-20 L ethanol at 60±5° C. for 90 minutes. This step was repeated twice and the resultant mixture was filtered and concentrated using rotary evaporation until the volume of the concentrated extract was about 30-70% of the original volume. Without dilution, the concentrated solution was then loaded onto a column packed with XAD1180N resin (a polystyrene divinyl-benzene copolymer resin). The column was eluted with an eluent solution containing ethanol and ethyl acetate at a volume ratio of about 1:1. The eluted fraction was collected and dried to produce a PA extract (yield: 1.1%)

Example 11: Exemplary *Plectranthus Amboinicus* Preparation Process K

For extraction, 1 kg of the above-ground part of *Plectranthus amboinicus* was stirred in 10-20 L ethanol at 60±5° C. for 90-180 minutes. The resultant mixture was filtered and concentrated using rotary evaporation until the volume of the concentrated extract was about 30-70% of the original volume. The concentrated solution was mixed with DIAION® HP-20 resin (a non-polar copolymer styrene-divynilbenzene adsorbent resin), which is then packed into a column. The column was eluted with an eluent solution containing ethanol and ethyl acetate at a volume ratio of about 1:1. The eluted fraction was collected and dried to produce a PA extract (yield: 1.0%)

Example 12: Exemplary *Plectranthus Amboinicus* Preparation Process L

For extraction, 1 kg of the above-ground part of *Plectranthus amboinicus* was stirred in 10-20 L ethanol at 60±5° C. for 90 minutes. The resultant mixture was filtered and concentrated using vacuum concentration until the volume is 30%-70% of the original volume. The concentrated solution was then loaded onto a column packed with DIAION® HP-20 resin (a non-polar copolymer styrene-divinylbenzene adsorbent resin). The column was eluted with an eluent solution containing ethanol and ethyl acetate at a volume ratio of about 1:1. The eluted fraction was collected and dried to obtain a PA extract (yield: 1.3%).

Example 13: Characterization of *Plectranthus Amboinicus* Extracts

The *Plectranthus amboinicus* extracts prepared by the above Examples were analyzed for the major phytochemicals contained therein by High Performance Liquid Chromatography (HPLC). The results are shown in Table 3 below.

The extracts prepared by Processes E, I, and J exhibited similar phytochemical compositions, indicating that different hydrophobic resins would yield similar *Plectranthus amboinicus* extracts The extracts prepared by Processes B and D exhibited similar phytochemical compositions, indicating that the use of eluent solutions of 50% acetone/50% ethyl acetate and 50% ethanol/50% ethyl acetate would yield similar *Plectranthus amboinicus* extracts.

Further, the extracts prepared by Processes E and K extraction process exhibited similar phytochemical compositions and the extracts prepared by Processes B, D, E and L with difference chromatographic separation processes also exhibited similar phytochemical compositions.

The characterization results also indicate that use of high extraction temperature (e.g., 60° C.±5° C.) can increase yield and decrease extraction time. In addition, a reduced level of concentration after extraction (e.g., reduction of volume to about 30-70% of the original volume) can substantially reduce the chromatographic separation time relative to a high level of concentration (e.g., reduction of volume to about 2.5-4% of the original volume), thereby substantially reduce the total time for preparing the extract. For example, Process E has a substantially reduced total preparation time prior to the chromatographic separation step (about 6 hours, including 3 hours extraction, 3 hours concentration) relative to Process F (about 57 hours, including 48 hours extraction and 9 hours concentration). Process E also has a shortened chromatographic separate step relative to Process F (6 hours v. 16 hours).

Further, performing the chromatographic separation process via mixing with the resin and filtration led to production of extracts having higher concentrations of active components as compared with column format (compare Process A with Process B or Process C with Process D).

TABLE 3

Characterization of *Plectranthus Amboinicus* Extracts

| | | Content, % | | | |
|---|---|---|---|---|---|
| Process | *Yield % | Salvigenin | Cirsimaritin | Rosmarinic acid | Carvacrol |
| A | 1.0% | 0.3 | 0.02 | 0.01 | 0.1 |
| B | 1.0% | 0.3 | 0.2 | 0.03 | 0.5 |
| C | 1.1% | 0.2 | 0.01 | 0.01 | 0.04 |
| D | 1.1% | 0.2 | 0.2 | 0.02 | 0.4 |
| E | 1.2% | 0.2 | 0.2 | 0.1-0.4 | 0.8-1.2 |
| F | 0.4% | 0.2 | 0.01 | N.D. | 0.05 |
| G | 1.4% | 0.3 | 0.7 | N.D. | 6.7 |
| H | 1.0% | 0.4 | 0.9 | 1.1 | 0.1 |
| I | 1.2% | 0.3 | 0.2 | 0.1 | 1.6 |
| J | 1.1% | 0.2 | 0.2 | 0.1 | 1.5 |
| K | 1.0% | 0.2 | 0.2 | 0.2 | 1.4-1.6 |
| L | 1.3% | 0.3 | 0.3 | 0.04 | 1.1 |

$$^*\text{Yield} = \frac{W(PA\ \text{extract})}{W(Plectranthus\ amboinicus)} \times 100\%$$

Example 14. Additional Exemplary Preparation Processes for Producing PA Extracts This example provides additional exemplary preparation processes for producing PA extracts, all of which are within the scope of the present disclosure.

In these exemplary preparation processes, the above-ground part of *Plectranthus amboinicus* was extracted using a solvent having a polarity index ranging from 4.3-6.6 at 25-60° C. for 1-3 hours. The extracting step was repeated for 1-3 times. The resultant crude extract was concentrated by 6 folds or by 50 folds. Alternatively, the resultant crude extract was not concentrated. Either the concentrated or the non-concentrated extract was then brought into contact with a suitable hydrophobic interaction chromatography resin (e.g., HP20, LX-20, or XAD1180N), e.g., loaded onto a column comprising the resin, or mixed with the resin for binding (the mixtures were stirred in some instances). The extract was then eluted from the resin using an eluent solution with a polarity index of 4.3-5.4.

Table 4 below summarizes reagents and conditions for each step in the exemplary preparation processes. Table 5 summarizes results from these preparation processes. The PA extracts prepared by the exemplary preparation processes contain about 0.04%-0.2% salvigenin, about 0.1%-0.3% cirsimaritin, about 0-0.3% rosmarinic acid, and about 0.3%-1.7% carvacrol.

TABLE 4

Exemplary PA Extract Preparation Processes

| Process | Extracting Solution | Tm (° C.) | Extracting Period (hour) | Extraction repeated time | Concentration (fold) | Resin | Absorption Manner | Eluent Solution |
|---|---|---|---|---|---|---|---|---|
| 1 | MeOH | 25 | 1 | 1 | 6 | HP-20 | Loading | EtOH/EA |
| 2 | Acetone | 25 | 2 | 2 | 6 | LX-20 | Binding | EA/Acetone |
| 3 | EA | 25 | 3 | 3 | 6 | XAD1180N | Stirring | Acetone/IPA |
| 4 | Acetone | 40 | 1 | 1 | 6 | XAD1180N | Binding | Acetone/IPA |
| 5 | EA | 40 | 2 | 2 | 6 | HP-20 | Stirring | EA/EtOH |
| 6 | MeOH | 40 | 3 | 3 | 6 | LX-20 | Loading | EA/Acetone |
| 7 | MeOH | 60 | 1 | 2 | 6 | LX-20 | Stirring | Acetone/IPA |
| 8 | Acetone | 60 | 2 | 3 | 6 | XAD1180N | Loading | EA/EtOH |
| 9 | EA | 60 | 3 | 1 | 6 | HP-20 | Binding | EA/Acetone |
| 10 | EA | 25 | 3 | 1 | No | LX-20 | Binding | EA/EtOH |
| 11 | MeOH | 25 | 2 | 1 | No | XAD1180N | Stirring | EA/Acetone |
| 12 | Acetone | 25 | 3 | 2 | No | HP-20 | Loading | Acetone/IPA |
| 13 | EA | 40 | 1 | 2 | No | XAD1180N | Loading | EA/Acetone |
| 14 | MeOH | 40 | 2 | 3 | No | HP-20 | Binding | Acetone/IPA |
| 15 | Acetone | 40 | 3 | 1 | No | LX-20 | Stirring | EA/EtOH |
| 16 | Acetone | 60 | 1 | 3 | No | HP-20 | Stirring | EA/Acetone |
| 17 | EA | 60 | 2 | 1 | No | LX-20 | Loading | Acetone/IPA |
| 18 | MeOH | 60 | 3 | 2 | No | XAD1180N | Binding | EA/EtOH |
| 19 | IPA | 60 | 1.5 | 2 | 6 | HP-20 | Binding | EA/EtOH |
| 20 | MeOH | 60 | 1.5 | 2 | 6 | HP-20 | Binding | EA/EtOH |
| 21 | Acetone | 60 | 1.5 | 2 | 6 | HP-20 | Binding | EA/EtOH |
| 22 | EA | 60 | 1.5 | 2 | 6 | HP-20 | Binding | EA/EtOH |

TABLE 5

Characterization of *Plectranthus Amboinicus* Extracts Prepared by Exemplary Processes

| | | Content (%) | | | |
|---|---|---|---|---|---|
| Process | Yields | Salvigenin | Cirsimaritin | Rosmarinic acid | Carvacrol |
| 1 | 0.9% | 0.2 | 0.2 | 0.1 | 0.8 |
| 2 | 0.2% | 0.1 | 0.1 | 0.04 | 1.6 |
| 3 | 0.3% | 0.1 | 0.1 | 0.006 | 1.0 |
| 4 | 0.3% | 0.1 | 0.1 | 0.1 | 1.5 |
| 5 | 0.3% | 0.1 | 0.1 | ND | 1.3 |
| 6 | 1.6% | 0.2 | 0.3 | 0.2 | 0.6 |
| 7 | 1.7% | 0.1 | 0.2 | 0.2 | 0.7 |
| 8 | 0.5% | 0.1 | 0.1 | 0.1 | 1.7 |
| 9 | 0.4% | 0.1 | 0.1 | ND | 1.1 |
| 10 | 0.1% | 0.04 | 0.1 | 0.006 | 0.6 |
| 11 | 0.9% | 0.1 | 0.1 | 0.1 | 0.8 |
| 12 | 0.2% | 0.1 | 0.1 | 0.04 | 1.3 |
| 13 | 0.2% | 0.1 | 0.1 | 0.01 | 1.1 |
| 14 | 1.0% | 0.1 | 0.1 | 0.1 | 0.3 |
| 15 | 0.3% | 0.1 | 0.2 | 0.2 | 1.7 |
| 16 | 0.2% | 0.1 | 0.2 | 0.3 | 1.5 |
| 17 | 0.5% | 0.1 | 0.2 | 0.1 | 1.5 |
| 18 | 1.4% | 0.2 | 0.2 | 0.2 | 0.5 |
| 19 | 0.8% | 0.2 | 0.1 | 0.02 | 0.5 |
| 20 | 1.5% | 0.2 | 0.2 | 0.1 | 0.7 |
| 21 | 0.4% | 0.1 | 0.1 | 0.1 | 1.3 |
| 22 | 0.3% | 0.2 | 0.2 | 0.02 | 1.6 |

* ND: not detected

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the claims.

EQUIVALENTS

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

All definitions, as defined and used herein, should be understood to control over dictionary definitions, definitions in documents incorporated by reference, and/or ordinary meanings of the defined terms.

All references, patents and patent applications disclosed herein are incorporated by reference with respect to the subject matter for which each is cited, which in some cases may encompass the entirety of the document.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

The term "about" or "approximately" means within an acceptable error range for the particular value as determined by one of ordinary skill in the art, which will depend in part on how the value is measured or determined, i.e., the limitations of the measurement system. For example, "about" can mean within an acceptable standard deviation, per the practice in the art. Alternatively, "about" can mean a range of up to ±20%, preferably up to ±10%, more preferably up to ±5%, and more preferably still up to ±1% of a given value. Alternatively, particularly with respect to biological systems or processes, the term can mean within an order of magnitude, preferably within 2-fold, of a value. Where particular values are described in the application and claims, unless otherwise stated, the term "about" is implicit and in this context means within an acceptable error range for the particular value. In some embodiments, the hinge domain is a hinge domain of a naturally occurring protein.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

What is claimed is:

1. A method for preparing a *Plectranthus amboinicus* extract consisting essentially of:
   (i) mixing leaves, stems, flowers, or a combination thereof of *Plectranthus amboinicus* with an extracting solution at 40° C.-80° C. for 1 hour-9 hours or at 20° C.-30° C. for 12 hours-48 hours to produce a first *Plectranthus amboinicus* extract;
   (ii) filtrating the first *Plectranthus amboinicus* extract or filtrating and concentrating the first *Plectranthus amboinicus* extract to produce a second *Plectranthus amboinicus* extract;
   (iii) contacting the second *Plectranthus amboinicus* extract onto a hydrophobic interaction chromatography resin, and
   (iv) eluting the column with an eluent solution to produce the *Plectranthus amboinicus* extract;
   wherein the extracting solution consists essentially of a solvent selected from the group consisting of ethanol, ethyl acetate, acetone, isopropyl alcohol, methanol, 1-butanol, i-butyl alcohol, methyl acetate, and methyl ethyl ketone;
   wherein the elution solution contains a mixture of at least two solvents selected from the group consisting of acetone, ethanol, ethyl acetate, isopropanol, and hexane; and
   wherein the hydrophobic interaction chromatography resin is selected from the group consisting of non-polar copolymer styrene divynilbenzene adsorbent resin, polystyrene polymer cross linked with divinylbenzene, polystyrene divinyl benzene copolymer resin and silica gel.

2. The method of claim 1, wherein step (ii) is performed by filtrating and concentrating the first *Plectranthus amboinicus* extract to produce the second *Plectranthus amboinicus* extract, which is a concentrated *Plectranthus amboinicus* extract.

3. The method of claim 1, wherein step (ii) is performed by filtering the first *Plectranthus amboinicus* extract to produce the second *Plectranthus amboinicus* extract.

4. The method of claim 1, wherein the solvent in the extracting solution is acetone, butyl methyl ether, ethanol, ethyl acetate, isopropyl alcohol, methanol, or a mixture thereof.

5. The method of claim 4, wherein the solvent is ethanol.

6. The method of claim 1, wherein step (i) is repeated 2-4 times.

7. The method of claim 6, wherein step (i) is repeated 2 times.

8. The method of claim 1, wherein step (i) is performed at a temperature of 50° C.-80° C. for about 1-9 hours.

9. The method of claim 1, wherein step (i) is performed at a temperature of 50° C.-80° C. for 1-3 hours.

10. The method of claim 9, wherein step (i) is performed at a temperature of 20° C.-30° C. for 12-24 hours.

11. The method of claim 1, wherein in step (i), the weight-to-volume ratio between the above-ground part of *Plectranthus amboinicus* and the extracting solution is 1:10 to 1:20 (kg/liter).

12. The method of claim 2, wherein in step (ii), the first *Plectranthus amboinicus* extract is concentrated to produce the concentrated *Plectranthus amboinicus* extract, and wherein the volume of the concentrated *Plectranthus amboinicus* extract is about 30% to 70% of the volume of the first *Plectranthus amboinicus* extract.

13. The method of claim 2, wherein in step (ii), the first *Plectranthus amboinicus* extract is concentrated to produce the concentrated *Plectranthus amboinicus* extract, and wherein the volume of the concentrated *Plectranthus amboinicus* extract is about 2.5% to 4% of the first *Plectranthus amboinicus* extract.

14. The method of claim 2, wherein step (iii) is performed by loading the concentrated *Plectranthus amboinicus* extract onto a column containing the hydrophobic interaction chromatography resin.

15. The method of claim 2, wherein step (iii) is performed by mixing the concentrated *Plectranthus amboinicus* extract with the hydrophobic interaction chromatography resin to allow for binding of components in the concentrated *Plectranthus amboinicus* extract to the hydrophobic interaction chromatography resin.

16. The method of claim 2, wherein step (iii) is performed by mixing the concentrated *Plectranthus amboinicus* extract with the hydrophobic interaction chromatography resin to form a mixture and stirring the mixture to allow for binding of components in the concentrated *Plectranthus amboinicus* extract to the hydrophobic interaction chromatography resin.

17. The method of claim 1, wherein the eluent solution is a mixture of two solvents at a 50:50 ratio by volume.

18. The method of claim 1, wherein the elution solution is selected from the group consisting of:
   (a) hexane and ethyl acetate,
   (b) ethanol and ethyl acetate,
   (c) acetone and ethyl acetate, and
   (d) acetone and isopropyl alcohol.

19. The method of claim 1, wherein the method further consists essentially of, prior to step (iv) and after step (iii), washing the hydrophobic interaction chromatography resin with an aqueous solution of ethanol.

* * * * *